Figure 1:
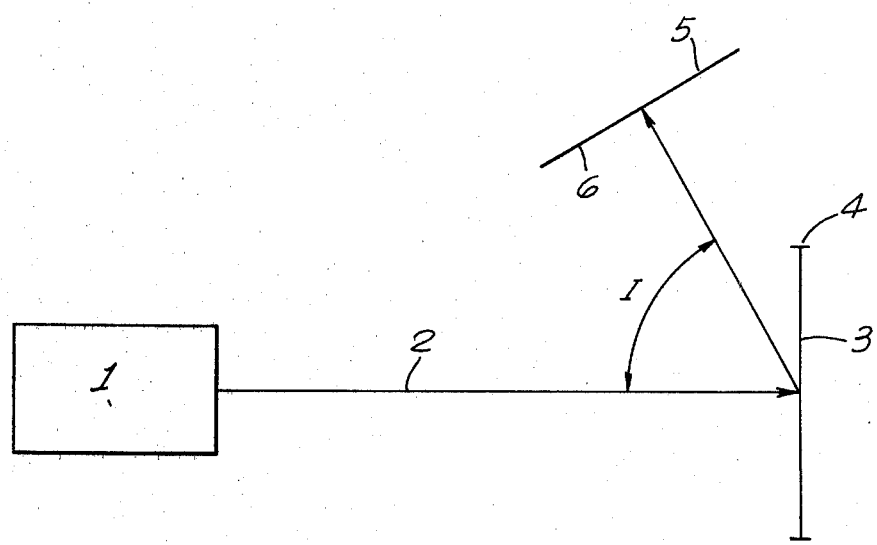

United States Patent [19]

Hershel et al.

[11] 4,453,828

[45] Jun. 12, 1984

[54] APPARATUS AND METHODS FOR MEASURING THE OPTICAL THICKNESS AND INDEX OF REFRACTION OF THIN, OPTICAL MEMBRANES

[75] Inventors: Ronald S. Hershel, Albany, Oreg.; Ray Winn, Studio City, Calif.

[73] Assignee: Advanced Semiconductor Products, Inc., Santa Cruz, Calif.

[21] Appl. No.: 326,488

[22] Filed: Dec. 2, 1981

[51] Int. Cl.³ ............................................. G02B 11/06
[52] U.S. Cl. ..................................... 356/357; 356/382
[58] Field of Search .......................... 356/357, 381, 382

[56] References Cited

U.S. PATENT DOCUMENTS 3,612,692 10/1971 Kruppa et al. ....................... 356/357

OTHER PUBLICATIONS

Bukreer et al., "A Laser Interference Thickness Gage", *Measurement Techniques*, vol. 18, No. 6, pp. 821–823, Jun. 1975.

Born et al., *Principles of Optics*, Pergamon Press, 1959, p. 16.

*Primary Examiner*—R. A. Rosenberger
*Attorney, Agent, or Firm*—Kendrick, Netter & Bennett

[57] ABSTRACT

A method for measuring accurately the optical thickness and index of refraction of thin, optical membranes includes directing light onto the membrane at one or more known angles of incidence, finding at least one angle of incidence, called a null angle, where the membrane reflects substantially none of the incident light, then calculating the optical thickness of the membrane, its index of refraction, or both, from one or more such null angles. Apparatus for this purpose includes means for directing a light beam onto thin, optical membranes, means for varying the angle of incidence of a light beam upon the membrane, and means for detecting the angles of incidence of the light beam on the membrane, including the null angles.

3 Claims, 1 Drawing Figure

APPARATUS AND METHODS FOR MEASURING THE OPTICAL THICKNESS AND INDEX OF REFRACTION OF THIN, OPTICAL MEMBRANES

This invention relates to methods and apparatus for measuring accurately the optical thickness and the index of refraction of thin, optical membranes. These membranes, and the methods and apparatus for making them, are the subject of copending U.S. patent application Ser. No. 326,489, filed the same day as this application, and entitled, "Thin Optical Membranes and Methods and Apparatus for Making Such Membranes." By this reference, we incorporate the entire disclosure of that application in this application.

Our methods for measuring accurately the optical thickness and the index of refraction of a thin, optical membrane comprise directing the light onto the membrane at one or more known angles of incidence; finding at least one angle of incidence, called a null angle, where the membrane reflects substantially none of the incident light; and then calculating the optical thickness of the membrane, its index of refraction, or both, from one or more such null angles.

The light can be laser light from such sources as helium-neon lasers. Such lasers produce collimated light beams with a wavelength of about 633 nanometers. Other high or even low intensity light sources may also be used, especially where detection of the null angles is made other than by unaided eyesight. Examples include filtered mercury arc lamps, filtered incandescent lamps, and filtered xenon lamps.

Visual detection of null angles is practicable where the light source has sufficient intensity to produce a reflected light beam of visually-perceptible intensity. Helium-neon laser light, for example, produces visually-detectable reflections. Moreover, because the accuracy of null angle detection is independent of the angle of incidence, visual detection of null angles is highly reliable. Where light sources other than laser light or high-intensity light sources are used, however, the detection of null angles by means of detectors such as photomultipliers, silicon PIN diodes, and other photovoltaic detectors may be necessary.

Our method not only permits measuring the optical thickness and index of refraction of thin, optical membranes, but can be used to monitor optical thickness of thin, optical membranes as well. Thus, for example, where thin, optical membranes are intended to have an optical thickness within specified limits, our method can monitor compliance with the specifications. To do so, we determine the angle of incidence at which membranes within the specified limits produce a null angle. We then test each membrane to see whether or not it produces a null at that angle.

In one embodiment of our method, we direct a beam of collimated laser light onto a thin, optical membrane at several different known angles of incidence. Preferably, we hold the light source fixed, and rotate the membrane in the path of the light beam to change the angle of incidence. A device such as a vernier joined to the means for rotating the membranes permits measurement of the angles of incidence.

Preferably, we begin the measurement procedure at a zero angle of incidence, and then rotate the thin, optical membrane to change the angle of incidence until we find the first angle where the membrane reflects no light. For some purposes, we may need to find more than one null angle. To do so, we continue rotating the membrane until we find a second null angle.

After we find at least one null angle of incidence, we calculate the thickness of the membrane from the following expressions (1): $Nt = k\lambda/4$. In expression (1), t is the thickness of the membrane; $\lambda$ is the wavelength of the incident light, typically measured in the same units as t; and k is the optical thickness of the membrane in units of quarter wavelengths of light. We call N the reduced index of refraction of the membrane, and calculate this reduced index of refraction from the following expression (2): $N = \sqrt{N^2 - (\sin I)^2}$, where N is the index of refraction of the membrane, and I is the null angle of incidence. To calculate thickness t from expression (1), we must know both N and k.

If we know the index of refraction of the membrane, but do not know k, we must find two consecutive null angles I1 and I2 for the membrane, and then compute thickness "t" from the following expression (3): $(N1 - N2)t = \lambda/2$. N1 is computed as follows: $N1 = \sqrt{N^2 - (\sin I1)^2}$. N2 is computed as follows: $N2 = \sqrt{N^2 - (\sin I2)^2}$.

Where we do not know the membrane's index of refraction N, but do know k, we must again find two consecutive null angles I1 and I2 for the membrane, and can then compute thickness t from the following expression (4): $t\sqrt{(\sin I2)^2 - (\sin I1)^2} = \lambda\sqrt{(k-1)}$. After calculating thickness "t", we can then calculate the index of refraction from expression (1). We can also calculate k from expression (4) if we know t.

The apparatus of our invention includes means for directing a light beam onto thin, optical membranes; means for varying the angle of incidence of the light beam upon the membrane; and means for detecting the angles of incidence and, in particular, the null angles.

FIG. 1 illustrates schematically one embodiment of this apparatus. In FIG. 1, helium/neon laser beam generator 1 directs a beam of collimated light 2 onto thin, optical membrane 3 at a known angle of incidence I. Rotatable fixture 4 holds membrane 3 in the path of beam 2, and permits rotation of fixture 4 and membrane 3 to a plurality of known angles of incidence. Screen 5, placed near fixture 4, has a reflective inner surface 6, which receives reflected light from membrane 3. Vernier markings on surface 6 permit detection of the angles of incidence.

Our new method and apparatus offers significant advantages over the known methods of measuring thickness of thin, optical films, namely spectrophotometry and ellipsometry. Spectrophotometry requires far more costly equipment than our methods and apparatus to measure the change in transmission or reflection of light at normal incidence as a function of the wavelength of incident light. From this change, the optical thickness at a given wavelength can be accurately measured. However, spectrophotometry does not permit measurement of the index of refraction. Ellipsometry also requires more expensive apparatus than our new apparatus, and is unreliable for measuring the thickness of unsupported, thin, optical membranes.

Our new method and apparatus are far less costly than spectrophotometers or even ellipsometers, and provide accurate measurements of the thickness and index of refraction of optical membranes simply, rapidly and at low cost.

The thin, optical membranes disclosed and claimed in copending U.S. patent application Ser. No. 326,489, filed the same day as this application, entitled, "Thin Optical Membranes and Methods and Apparatus for Making Such Membranes," and referred to above, have new uses not disclosed there. These membranes exhibit excellent elasticity and homogeneity. In particular, these membranes can be used to copy and reproduce large quantities of data in compressed form and with substantially no distortion, especially where these membranes are mounted on mechanically, thermally stable frames or other supports. To effect this copying, we simply form the thin, optical membranes on a surface which carries a large quantity of data in highly compressed form. Our membranes form an accurate, precise duplicate of the data from the original, and can then be utilized as an original for replication and for storage of the data.

In one embodiment, we form a thin, optical membrane on a surface carrying large quantities of data in compressed form as an embodiment on the surface. By forming the thin, optical membrane on such embossed surfaces, we replicate identically the surface embossment and the data contained in that embossment.

Our data-carrying, thin, optical membranes have a nominal thickness in the range of about 0.5 to about 10 micrometers, and exhibit edge-to-edge variations in nominal thickness of less than about 2%, and preferably about less than 1%. In any one membrane, variations in nominal thickness from edge to edge of the membrane can be limited to less than about 2%, and preferably less than about 1%. Unit-to-unit variations in nominal thickness of these membranes can be limited to less than about 2%, and preferably less than about 1%.

These membranes are highly light-transmissive. Specifically, these membranes transmit in the range of about 84% to about 99% of incident light and can be made to transmit at least about 96%, 98% or even 99% of incident light at one or more wavelengths of light in the range of about 260 to about 1,000 nanometers. Yet, these membranes shift the focus of incident light in an optical path less than about a third of the membrane's thickness. Because the membranes are highly light-transmissive, they absorb, diffract and disperse less than about 3% of incident light, and can be made to absorb, diffract and disperse less than about 1% of incident light at one or more specific wavelengths in the range of about 260 to about 1,000 nanometers (nm).

What is claimed is:

1. A method comprising directing light onto a thin, optical membrane at one or more known angles of incidence, said membrane having a thickness in the range of about 0.5 to about 10 micrometers, said membrane being capable of being edge-supported; finding two consecutive null angles of incidence for said membrane; calculating the thickness t of said membrane from the expression: $t\sqrt{(\sin I2)^2 - (\sin I1)^2} = (\lambda/2)\sqrt{k-1}$, where I2 and I1, are said two consecutive null angles of incidence for said membrane, $\lambda$ is the wavelength of the incident light, and k is an assumed, even integer value, in quarter wavelengths of light, for the optical thickness of said membrane; then calculating the index of refraction N of said membrane from the calculated value of t and the assumed value of k in the expression: $Nt = k(\lambda/4)$, where N is equal to the square root of the expression $N^2 - (\sin I)^2$, I is I1 or I2, and N is the index of refraction for said membrane.

2. A method comprising directing light onto a thin, optical membrane at one or more known angles of incidence, said membrane having a thickness in the range of about 0.5 to about 10 micrometers, said membrane being capable of being edge-supported; finding two consecutive null angles of incidence for said membrane; calculating the thickness t of said membrane from the expression: $t\sqrt{(\sin I2)^2 - (\sin I1)^2} = (\lambda/2)\sqrt{k-1}$, where I2 and I1 are said two consecutive null angles of incidence for said membrane, $\lambda$ is the wavelength of the incident light, and k is an assumed, even integer value, in quarter wavelengths of light, for the optical thickness of said membrane; then calculating the index of refraction N of said membrane from the calculated value of t and the assumed value of k in the expression $Nt = k(\lambda/4)$, where N is equal to the square root of the expression $N^2 - (\sin I)^2$, I is I1 or I2 and N is the index of refraction for said membrane; then directing light onto another thin, optical membrane having a thickness in the range of about 0.5 to about 10 micrometers, and being capable of being edge-supported, at a null angle of incidence for said other membrane; and then calculating the thickness t of said other membrane from the expression $Nt = k\lambda/4$ where $\lambda$ is the wavelength of the incident light; k is said assumed, even integer value, in quarter wavelengths of light, for the optical thickness of said membrane; N is equal to the square root of the expression $N^2 - (\sin I)^2$; and N is said calculated value of the index of refraction of said membrane, and most closely approximates the nominal value of the index of refraction for said membrane.

3. A method comprising directing light onto a thin, optical membrane at one or more known angles of incidence, said membrane having a thickness in the range of about 0.5 to about 10 micrometers, said membrane being capable of being edge-supported; finding two consecutive null angles of incidence for said membrane; calculating the thickness t of said membrane from the expression: $t\sqrt{(\sin I2)^2 - (\sin I1)^2} = (\lambda/2)\sqrt{k-1}$, where I2 and I1 are said two consecutive null angles of incidence for said membrane, $\lambda$ is the wavelength of the incident light, and k is an assumed, even integer value, in quarter wavelengths of light, for the optical thickness of said membrane s; then calculating the index of refraction N of said membrane from the calculated value of t and the assumed value of k in the expression $Nt = k(\lambda/4)$, where N is equal to the square root of the expression $N^2 - (\sin I)^2$, I is I1 or I2, and N is the index of refraction for said membrane; then directing light onto another thin, optical membrane having a thickness in the range of about 0.5 to about 10 micrometers and being capable of being edge-supported; finding two consecutive null angles of incidence for said other membrane; computing the thickness t of said other membrane from the expression $(N3 - N4)t = \lambda/2$ where $N3 = \sqrt{N^2 - (\sin I3)^2}$; and $N4 = \sqrt{N^2 - (\sin I4)^2}$; I3 is the first null angle of incidence for said other membrane; I4 is the second null angle for said other membrane; $\lambda$ is the wavelength of the incident light striking said other membrane; and N is said calculated value of the index of refraction of said membrane and most closely approximates the nominal value of the index of refraction for said membrane.

* * * * *